United States Patent [19]
Sage, Jr.

[11] Patent Number: 5,256,137
[45] Date of Patent: Oct. 26, 1993

[54] BIPHASIC POWER SOURCE FOR USE IN AN IONTOPHORETIC DRUG DELIVERY SYSTEM

[75] Inventor: Burton H. Sage, Jr., Raleigh, N.C.

[73] Assignee: Becton Dickinson and Company, Franklin Lakes, N.J.

[21] Appl. No.: 848,217

[22] Filed: Mar. 10, 1992

[51] Int. Cl.5 .............................................. H61N 1/30
[52] U.S. Cl. ...................... 604/20; 607/149
[58] Field of Search ............... 604/20; 128/798, 802, 128/803

[56] References Cited

U.S. PATENT DOCUMENTS

| | | | |
|---|---|---|---|
| H516 | 9/1988 | Lattin et al. | 604/20 |
| 3,991,755 | 11/1976 | Vernon et al. | 128/789 |
| 4,141,359 | 2/1979 | Jacobsen et al. | 604/20 |
| 4,164,226 | 8/1979 | Tapper | 604/20 |
| 4,211,222 | 7/1980 | Tapper | 604/20 |
| 4,292,968 | 10/1981 | Ellis | 604/20 |
| 4,456,012 | 6/1984 | Lattin | 604/20 |
| 4,457,748 | 7/1984 | Lattin et al. | 128/760 |
| 4,725,263 | 2/1988 | McNichols et al. | 604/20 |
| 4,764,164 | 8/1988 | Sasaki | 604/20 |
| 5,042,975 | 8/1991 | Chien et al. | 604/20 |
| 5,047,007 | 9/1991 | McNichols et al. | 604/20 |

FOREIGN PATENT DOCUMENTS 01939 3/1991 PCT Int'l Appl. ............... 604/20

OTHER PUBLICATIONS

*Altered Epidermal Morphology Secondary to Lidocaine Iontophoresis: In Vivo and In Vitro Studies in Porcaine Skin,* by Nancy Monteiro-Riviere, Fundamental Applied Technology, vol. 15, pp. 174–185 (1990).

Primary Examiner—C. Fred Rosenbaum
Assistant Examiner—Michael Rafa
Attorney, Agent, or Firm—Hoffmann & Baron

[57] ABSTRACT

A biphasic power source for use in an iontophoretic system, which system includes a transdermal drug delivery device attachable to a patient and having a positive electrode and a negative electrode, includes a constant current source and a voltage limiting circuit. The constant current source has two outputs and provides a constant current on the outputs. The outputs are connected to the positive and negative electrodes of the transdermal drug delivery device. The voltage limiting circuit is connected in parallel with the outputs of the constant current source to limit the voltage across the electrodes to a predetermined voltage. The voltage limiting circuit may be a zener diode.

7 Claims, 3 Drawing Sheets

BIPHASIC POWER SOURCE FOR USE IN AN IONTOPHORETIC DRUG DELIVERY SYSTEM

BACKGROUND OF THE INVENTION

1. Field of the Invention

This invention generally relates to a system and method for iontophoretic drug delivery having features for reducing irritation to the skin of an animal and more particularly to a system and method for delivery of power during iontophoretic drug delivery in a sequence for reducing skin irritation.

2. Description of the Prior Art

Iontophoresis is gaining increased acceptance as an effective method for application of ionic agents or ionic drugs through the skin of an animal. Iontophoresis can be defined as the electrically driven application of drugs or medications, in their ionic form, to the surface tissues of an animal. The application of electric current causes migration of ions into the tissue wherein such migration is proportional to the quantity of current applied through the iontophoretic system.

Skin irritation can occur during iontophoretic drug delivery. Efforts to minimize irritation have been directed to regulating the level of current, improving the electrical connection of the electrode with the skin and reducing the hydrolysis of water in the ionic medication. Irritation of the skin may be subjective wherein the iontophoretic electrode delivers so much power that it causes extreme discomfort to the patient. There are also objective indicia of irritation such as petechia, erythema and edema. Occurrence of such forms of irritation is discussed by Nancy A. Monteiro-Riviere in a paper presented in *Fundamental Applied Technology*, entitled "Altered Epidermal Morphology Secondary to Lidocaine Iontophoresis: In Vivo and In Vitro Studies in Procaine Skin", Vol. 15, pages 174–185 (1990).

It is known that the impedance of a patient's skin can range from over 100,000 ohms to nearly 1000 ohms, depending on the duration that the iontophoretic current is applied, the magnitude of the current which is being delivered, the location of the system on the patient's body, and other factors. In a system where the desired current level, which is determined in part by the drug administered to the patient, is one milliamp, a voltage potential of 100 volts would result if the skin impedance is 100,000 ohms. Since such a voltage would cause undesirable sensations to the user, it is highly desirable to limit the voltage across the electrodes of the iontophoretic drug delivery device to a more tolerable level.

Numerous prior art references attempt to teach iontophoretic devices which attempt to avoid irritation and/or tissue damage. For example, U.S. Pat. No. 4,292,968 to Ellis discloses an apparatus for delivering constant current during ion therapy (iontophoresis) which will abruptly switch to delivering constant voltage when the voltage across the electrodes reaches a predetermined level. Thus, the Ellis patent discloses a dual mode power source for an iontophoretic system.

However, the dual mode power source described in the Ellis patent is impractical for use with a transdermal drug delivery system. The Ellis power source employs a voltage limit of 1.1 volts. While skin impedance levels in man can range as low as 1,000 ohms, more typical values during drug delivery are in the range of 5,000–10,000 ohms. This leaves a current typically in the range of 100 to 200 $\mu$A, a level which will fail to deliver much drug.

Also, the Ellis dual mode power source first provides a constant current to the electrodes of the drug delivery device, and then switches to a constant voltage if the voltage across the electrodes exceeds 1.1 volts. As described in the present invention, it is the opposite sequence, that is, changing from a constant voltage to a constant current, which is important in reducing skin irritation and burning.

U.S. Pat. No. 4,141,359 to Jacobsen et al. teaches an epidermal iontophoresis device which is capable of maintaining a constant current through the epidermal tissue. To prevent excessive voltage build-up and the accompanying dangers of shock and burns, a comparative circuit monitors current flow and voltage across the electrodes and automatically triggers an SCR shut down circuit when impedance readings are outside of predetermined limits.

The Jacobsen et al. patent thus describes an iontophoresis power source which is a constant current source with an output voltage capable of reaching 60 volts. There is no means to prevent the voltage from reaching this level which can cause adverse sensations to the patient. Described in this patent is a safety mechanism which is activated if the patch is removed while power is being delivered. This mechanism checks the impedance of the load and turns the system off if there is a large sudden change in the impedance.

As mentioned above, it is well known that undesirable sensations will arise when voltages of this level (60 volts) are applied to the skin. To avoid these sensations, the circuit described in the Jacobsen et al. patent provides for the user to set the level of controlled current, and in this way avoid the sensations. There is no provision for any automatic means to limit these sensations. Hence, by providing user control of the level of constant current, the Jacobsen et al. patent teaches away from the concept of a biphasic power source which utilizes the skin impedance to accomplish the phase transition.

Although the prior art is replete with devices for reducing skin irritation and skin damage, the prior art efforts appear to focus on the device itself. Devices running on lower voltages, devices having intermediate pads between the electrodes and the skin, devices producing pulsating current, and devices having large electrode areas to reduce current concentration all approach the problem from a device perspective. The prior art has not attempted to understand the resistivity of the skin and develop a system that can take advantage of the natural properties of the skin in order to optimize the iontophoretic delivery while minimizing irritation and skin damages.

OBJECTS AND SUMMARY OF THE INVENTION

It is an object of the present invention to provide a system and method for delivering a drug iontophoretically to an animal.

It is another object of the present invention to provide a biphasic power source which operates with a drug delivery device to control the amount of drug and the rate at which the drug is delivered.

It is a further object of the present invention to provide an iontophoretic drug delivery system which minimizes or eliminates undesirable irritation, burning and rubefaction of the skin of the animal to which the system is attached.

It is yet another object of the present invention to provide an electronic circuit which provides a constant voltage and constant current to the electrodes of an iontophoretic drug delivery device attachable to a patient.

It is still a further object of the present invention to provide an iontophoresis drug delivery system and method which overcomes the inherent drawbacks of known systems and methods.

In accordance with one form of the present invention, an iontophoretic drug delivery system includes a device having a drug reservoir adapted to be placed in communication with the skin of an animal and an electrolyte reservoir which is adapted to be placed in communication with the skin of the animal. The device includes two electrodes. The first electrode may be mounted at least partially in the drug reservoir, and the second electrode may be mounted at least partially in the electrolyte reservoir.

The drug delivery system includes a biphasic power source coupled to the electrodes of the device having the drug reservoir and the electrolyte reservoir, which power source provides at least one of a constant voltage and a constant current to the electrodes. The biphasic power source preferably includes a constant current source having two outputs connected to the electrodes of the drug delivery device, and a voltage limiting circuit, such as a zener diode, coupled in parallel with the outputs of the constant current source to limit the voltage across the electrodes to a predetermined voltage.

These and other objects, features and advantages of this invention will become apparent from the following detailed description of illustrative embodiments thereof, which is to be read in connection with the accompanying drawings.

DETAILED DESCRIPTION OF THE PREFERRED EMBODIMENTS

Figure 1:
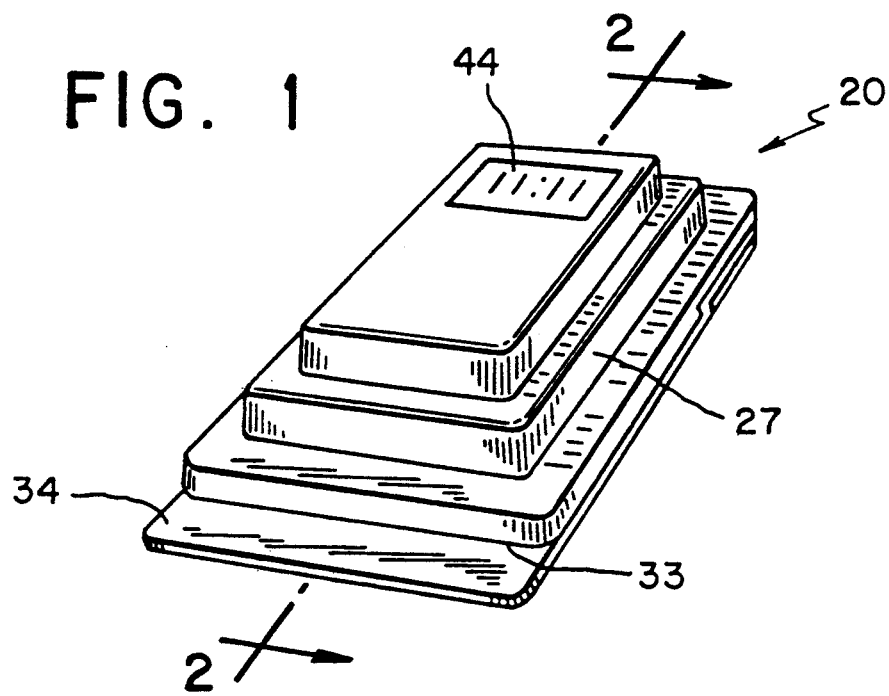
FIG. 1 is a perspective view of an iontophoretic drug delivery system of the present invention.

Referring initially to FIGS. 1-5, an operable iontophoretic drug delivery system/device 20 includes a drug reservoir 21 adapted to be attached to the skin of an animal, a first electrode 22 in the drug reservoir, an electrolyte reservoir 23 adapted to be attached to the skin of an animal and a second electrode 25 in the electrolyte reservoir.

For the purposes of the description of the present invention, the term "proximal" or "lower" is meant to refer to the side of the device closest to the skin, whereas the term "distal" or "upper" is meant to refer to the side of the device or element which is furthest from the skin.

For the purpose of description of the present invention and the claims, the term "animal" as used herein shall include all living beings including humans. The term "irritation" as used herein shall mean subjective irritation such as pain and tingling and objective irritation such as petechia, erythema and edema.

In this embodiment, drug reservoir 21 and electrolyte reservoir 23 are part of a common housing 27. First electrode 22 and second electrode 25 are electrically separated by insulating material 28 in the housing. In this embodiment, the entire housing is made of insulating material, such as plastic.

Drug reservoir 21 is capable of holding an ionic compound such as a therapeutic compound, a diagnostic compound and a drug. In many cases, the ionic compounds are ionic liquids, however, the compound may be in the form of a gel or may be contained in the reservoir along with other materials such as porous polymeric structures. For the purpose of the description of this invention, drug reservoir 21 contains a therapeutic liquid 29. This therapeutic liquid does not limit the invention but is intended to be representative of these many possibilities for an ionic compound which can be delivered iontophoretically.

Electrolyte reservoir 23 contains electrolyte solution 31. The electrolyte solution may be in the form of a liquid or a gel, or may be contained in the reservoir along with other materials such as porous polymeric material.

Lower surface 32 of the housing contains an adhesive coating 33 for attaching the housing to the skin of an animal. A removable release sheet 34 is provided to protect the adhesive before time of use and for helping to contain the therapeutic liquid and the electrolyte in the reservoirs before time of use.

Figure 2:
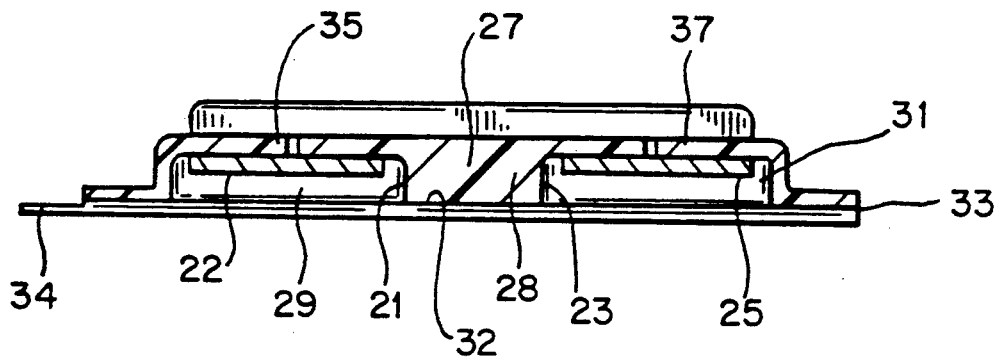
FIG. 2 is a partial cross-sectional view of the drug delivery device of FIG. 1 taken along line 2—2.

The drug delivery device shown in FIGS. 1 and 2 further includes conductors 35 and 37 which are respectively connected to electrodes 22 and 25 and to the electronic circuit of the iontophoresis system of the present invention.

Figure 6:
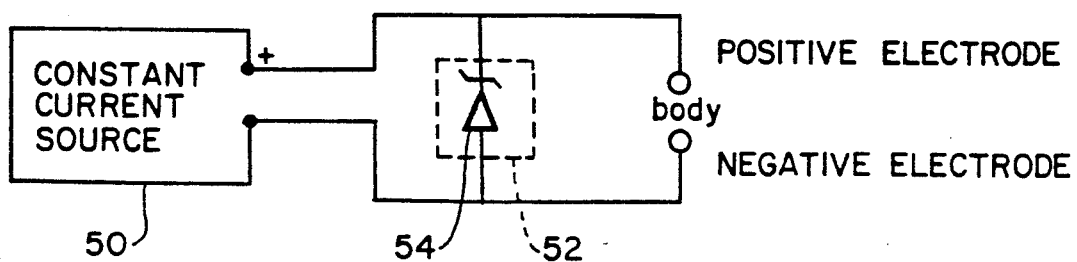
FIG. 6 is a block diagram view showing a biphasic power source of the present invention for providing a constant current and a constant voltage to the electrodes of a transdermal drug delivery device.

A substantial difference between the iontophoretic drug delivery device of the present invention and the prior art lies in the electronic circuitry, one form of which is shown in FIG. 6. To fully understand the major structural and functional differences between the device of the present invention and the prior art it is important to understand the properties of the skin into which ions are driven by an iontophoretic drug delivery device. The electrical impedance of the skin greatly affects the occurrence of irritation and tissue damage. The electrical impedance of epidermal tissue is highly variable, depending on such factors as location on the body, presence of calluses or dermal abrasions, ambient air conditions such as temperature and humidity, state of hydration which may be caused by perspiration, and the age, sex and race of the individual. It is known that the dose of an ionic substance delivered to an individual is in general proportional to the electric current. In efforts to increase the dose of ionic substance or reduce the time over which a given dose may be administered, the electric current is often raised to a level which results in skin irritation and skin damage including burns. For example, Jacobsen et al. in U.S. Pat. No. 4,141,359 cite native values of skin impedance of 10,000 to 50,000 ohms. If a modest current of 3 milliamperes is caused to flow through skin with an average value of 30,000 ohms, the required voltage by Ohms, Law would be 30,000 ohms time 0.003 amperes or 90 volts. Such a voltage is widely known to be capable of causing irreversible skin breakdown, which is believed to provide low resistance paths, and hence paths where high levels of energy are dissipated in the skin. This high level of energy is believed to cause burns.

During iontophoresis episodes, the impedance of skin through which ions are transferred is initially at a high value, and then steadily decreases. The instant invention provides a device and a method for effective iontophoretic delivery while minimizing irritation and burns by accommodating the highly variable nature of skin impedance.

Figure 3:
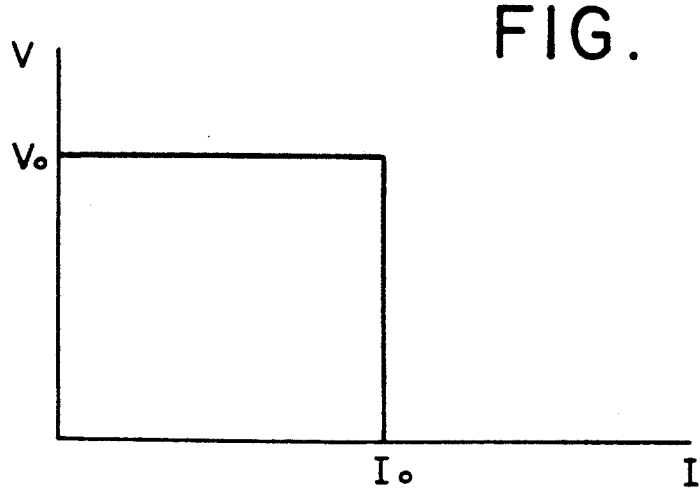
FIG. 3 is a graph illustrating voltage and current which demonstrate the operation of the present invention.
Figure 4:
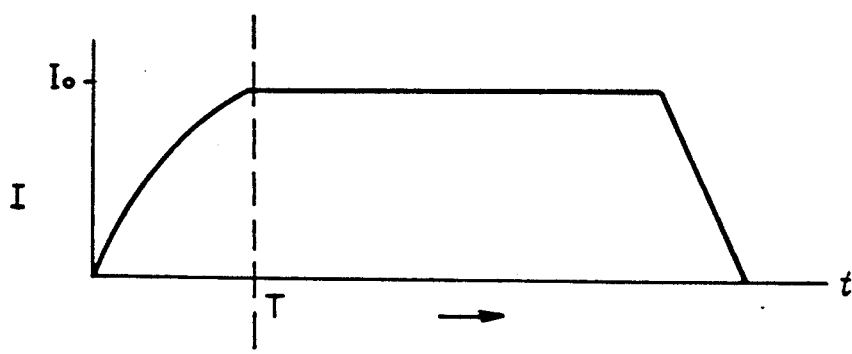
FIG. 4 is a graph illustrating a profile of current with respect to time for iontophoretic delivery of the present invention.
Figure 5:
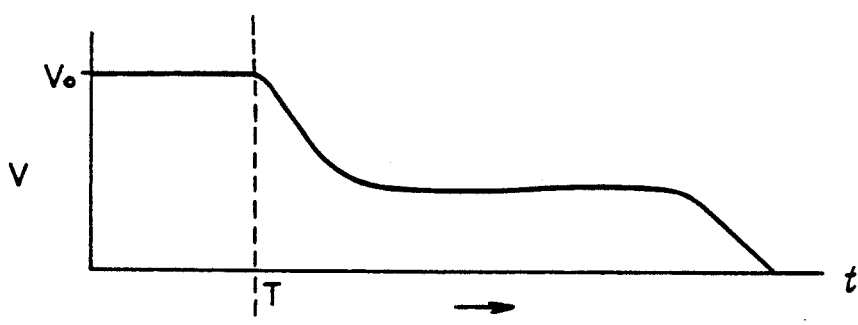
FIG. 5 is a graph illustrating voltage with respect to time for iontophoretic delivery using the present invention.

The method and the device of the instant invention work as follows. An iontophoretic delivery device such as device 20 is attached to the skin of an animal. The attachment can be accomplished by removing the backing sheet and pressing the device against the skin. Next, electrical power is caused to flow between the electrodes at a constant voltage $V_o$ as illustrated in FIGS. 3 and 5. $V_o$ is of a sufficiently low magnitude such as not to cause irritation to the skin. Because of the initial high impedance of skin, the current is at a low value during this time as illustrated in FIG. 4. Because current is flowing, the skin impedance begins to fall allowing more current to flow. This in turn causes the skin impedance to decrease further, which permits more current to flow, and so on as illustrated in FIG. 4. At time T in FIG. 4 the current reaches the pre-selected value of $I_o$. When $I_o$ is reached, the electronic circuit, supplying a constant voltage $V_o$ to the electrodes, as will be explained in more detail hereinafter, changes modes and becomes a constant current source (see FIGS. 4 and 5). FIG. 4 illustrates the rise of current to $I_o$ at which time current becomes constant at $I_o$. When $I_o$ is reached, and the system delivers constant current $I_o$, the voltage begins falling. This falling off of voltage from the $V_o$ value is due to the decreasing resistance of the skin. The instant invention functions such that the voltage is prevented from rising to a level which can cause irreversible skin breakdown which leads to burns. At the same time, the desirable constant current capability is provided once the changeover to $I_o$ is achieved. The electronic circuit thus changes from supplying a constant voltage $V_o$ to the electrodes to supplying a constant current $I_o$. This current continues to flow between the electrodes, at a constant predetermined rate, until the therapy regimen is completed.

It is known that there is a relationship between the current delivered to the electrodes and the quantity of ions transferred through the skin. Accordingly, the amount of current with respect to time can be measured to determine the amount of drug transferred through the skin. When using the method of the instant invention, the user can monitor the total current (over time) flowing between the electrodes and terminate power to the electrodes when the total amount of current, corresponding to the delivery of the desired amount of ionic compound into the skin, has been achieved.

A preferred form of the electronic circuit for providing a constant voltage and constant current to the electrodes of the drug delivery device 20 is the biphasic power source shown in FIG. 6. The biphasic power source includes a constant current source 50 having two outputs which are connected to the positive and negative electrodes 22 and 25 of the drug delivery device 20, and a voltage limiting circuit 52 connected in parallel with the outputs of the constant current source 50.

In one form of the invention, the voltage limiting circuit 52 is a zener diode 54 arranged with its anode connected to the negative electrode 25 and its cathode connected to the positive electrode 22.

The circuit operates in the following manner. When the iontophoresis system is first turned on, the skin impedance is very high. Since the power source is a constant current source, it puts out a given desired amount of current. If the zener diode 54 was not present, the voltage across the skin would be very large. With the zener diode present, the voltage rises until the zener diode starts to conduct. The zener diode 54 then passes all the current which the skin cannot conduct at that voltage, and thereby limits the voltage across the skin. As time passes, the skin impedance falls. At some point, when the skin impedance is sufficiently low, the skin can take all the current from the constant current source 50 at a voltage less than that of the zener diode 54. As far as the above circuit is concerned, the zener diode is now "out of the circuit" since the voltage is below the point where it conducts.

Thus, it can be seen that the biphasic power source of the present invention operates in two modes—a constant voltage mode and a constant current mode. Also, it should be noted that the mode change is dictated by the skin impedance of the animal. The biphasic power source supplies a constant voltage to the positive and negative electrodes 22, 25 when the skin impedance of the animal is at least equal to a predetermined level, and supplies a constant current to the electrodes when the skin impedance of the animal is less than the predetermined level.

The skin impedance at which one desires to switch modes is dependent upon a number of factors, including the effective area of the drug reservoir 21 in contact with the patient's skin, the magnitude of the constant current delivered to the drug reservoir over the effective skin contact area, and the voltage across the electrodes 22, 25 of the drug delivery device at the time of switching from the constant voltage mode to the constant current mode.

For example, if the drug reservoir skin contact area is 5 square centimeters and the current provided to the drug reservoir is 200 $\mu$a/square cm (for a total current of 1 ma), and the voltage across the electrodes at the time of switching modes is 6 volts, then the predetermined skin impedance is 6,000 ohms.

If, on the other hand, a 1 square centimeter (contact area) "patch" is employed which is driven by a current of 100 $\mu$a/square cm (for a total current 0.1 ma), and the voltage across the electrodes at the time of switching modes is 20 volts, then the predetermined skin impedance is 200K ohms for switching.

It has been found that the voltage during transdermal drug delivery treatment should be between about 3 and about 30 volts and, more preferably, between about 6 and about 20 volts to achieve effective drug delivery rates while avoiding discomfort to the patient. Accordingly, the zener diode 54 should be selected to have a breakdown voltage in those ranges. Of course, it is envisioned that other devices than zener diode 54 may be used for voltage limiting means 52. Such devices may include shunt regulators and other similarly performing devices. It is preferred if each of these devices limits the voltage on the electrodes to between about 3 and about 30 volts and, more preferably, between about 6 and about 20 volts, as mentioned previously.

Although illustrative embodiments of the present invention have been described herein with reference to the accompanying drawings, it is to be understood that the invention is not limited to those precise embodiments, and that various other changes and modifications may be effected there by one skilled in the art without departing from the scope or spirit of the invention.

What is claimed is:

1. An iontophoresis system for delivering therapeutic compounds to the skin of an animal, which comprises:
    a transdermal drug delivery device attachable to the animal and in communication with the skin thereof, the device including a first electrode and a second electrode, and reservoirs for containing an electrolyte and a therapeutic drug in electrical communication with the first and second electrodes;
    a biphasic power source connected to the first and second electrodes of the drug delivery device, the biphasic power source including means for providing a constant voltage, and means for providing a constant current, the constant current means and constant voltage means being connected to the electrodes of the drug delivery device;
    means for switching between said constant voltage providing means and said constant current providing means when the skin impedance of the animal is less than a predetermined level;
    wherein the biphasic power source is in a first mode and supplying a constant voltage to the first and second electrodes when the skin impedance of the animal is at least equal to a predetermined level, and wherein the biphasic power source is in a second mode and supplying a constant current to the first and second electrodes when the skin impedance of the animal is less than the predetermined level.

2. An iontophoresis system as defined by claim 1, wherein the constant voltage means limits the voltage across the first and second electrodes to between about 3 and about 30 volts.

3. An iontophoresis system as defined by claim 1, wherein the constant voltage means limits the voltage across the first and second electrodes to between about 6 and about 20 volts.

4. An iontophoresis system as defined by claim 1, wherein the means for providing a constant voltage includes a zener diode, and the first electrode is a positive electrode and the second electrode is a negative electrode, and wherein the zener diode has an anode connected to the negative electrode and a cathode connected to the positive electrode.

5. An iontophoresis system as defined by claim 4, wherein the zener diode is selected to have a breakdown voltage of between about 3 and about 30 volts.

6. An iontophoresis system as defined by claim 4, wherein the zener diode is selected to have a breakdown voltage of between about 6 and about 20 volts.

7. A method for providing power to electrodes of a transdermal drug delivery device attachable to the skin of an animal, the method comprising the steps of:
    supplying a constant voltage to the electrodes of the transdermal drug delivery device when the skin impedance of the animal is at least equal to a predetermined level; and
    supplying a constant current to the electrodes when the skin impedance of the animal is less than the predetermined level.

* * * * *